United States Patent
Miller (10) Patent No.: US 11,177,023 B2
(45) Date of Patent: *Nov. 16, 2021

(54) LINKING ENTITY RECORDS BASED ON EVENT INFORMATION

(71) Applicant: International Business Machines Corporation, Armonk, NY (US)

(72) Inventor: Jacob O. Miller, Cleveland, OH (US)

(73) Assignee: International Business Machines Corporation, Armonk, NY (US)

( * ) Notice: Subject to any disclaimer, the term of this patent is extended or adjusted under 35 U.S.C. 154(b) by 216 days.

This patent is subject to a terminal disclaimer.

(21) Appl. No.: 15/634,053

(22) Filed: Jun. 27, 2017

(65) Prior Publication Data

US 2017/0293724 A1    Oct. 12, 2017

Related U.S. Application Data (63) Continuation of application No. 14/988,009, filed on Jan. 5, 2016.

(51) Int. Cl.
*G16H 10/60* (2018.01)
*G16H 10/40* (2018.01)
*G06Q 10/10* (2012.01)

(52) U.S. Cl.
CPC ............. *G16H 10/60* (2018.01); *G06Q 10/10* (2013.01); *G16H 10/40* (2018.01)

(58) Field of Classification Search
CPC ................... G06Q 10/10; G06Q 40/00; G06Q 10/063112; G06Q 10/06314;
(Continued)

(56) References Cited

U.S. PATENT DOCUMENTS

| 5,692,125 | A | 11/1997 | Schloss et al. | |
| 5,784,635 | A * | 7/1998 | McCallum | ............ G06F 40/205 |
| | | | | 712/32 |
| 7,680,703 | B1 | 3/2010 | Smith | |
| 7,937,344 | B2 | 5/2011 | Baum et al. | |
| 2004/0199332 | A1* | 10/2004 | Iliff | ........................ G16H 10/60 |
| | | | | 702/19 |

(Continued)

FOREIGN PATENT DOCUMENTS

| WO | 2011042838 A1 | 4/2011 | |
| WO | WO-2011042838 A1 * | 4/2011 | ............. G06Q 10/06 |

OTHER PUBLICATIONS

Bai-Sheng Shi, A knowledge discovery technique for heterogeneous data sources; Feb. 2004 ; IEEE,https://iq.ip.com/npl/ieee/1264489 (Feb. 2004) (Year: 2004).*

(Continued)

*Primary Examiner* — Hiep V Nguyen
(74) *Attorney, Agent, or Firm* — Will Stock; Edell, Shapiro & Finnan, LLC (57) ABSTRACT

A system links data objects associated with a common event and includes at least one processor. The system compares data objects associated with an entity and corresponding to a plurality of events for the entity, wherein the data objects are stored within a plurality of different source systems. Candidate data objects associated with a common event for the entity are identified based on the comparing. The candidate data objects are linked to form a set of data objects representing the common event for the entity. Embodiments of the present invention further include a method and computer program product for linking data objects associated with a common entity.

4 Claims, 7 Drawing Sheets

(58) Field of Classification Search
CPC ......... G06Q 10/06398; G06Q 10/1093; G06Q 20/3829; G06Q 50/01; G06Q 50/22; G06Q 10/00; G06Q 30/04; G06Q 50/24; G06Q 50/26; G06Q 10/063; G06Q 10/0631; G06Q 10/06313; G06Q 10/06375; G06Q 10/0639; G06Q 20/06; G06Q 20/382; G06Q 20/389; G06Q 30/02; G06Q 30/0269; G06Q 30/0277; G06Q 30/0633; G06Q 30/0641; G06Q 30/08; G06Q 50/18; G06Q 90/20
USPC .......................................................... 705/2
See application file for complete search history.

(56) References Cited

U.S. PATENT DOCUMENTS

| | | | |
|---|---|---|---|
| 2006/0122807 A1* | 6/2006 | Wittkowski | G06F 17/18 702/179 |
| 2011/0243417 A1 | 10/2011 | Madabhushi et al. | |
| 2013/0080192 A1* | 3/2013 | Bucur | G06Q 50/24 705/3 |
| 2014/0006391 A1 | 1/2014 | Friedlander et al. | |
| 2014/0032240 A1 | 1/2014 | Lougheed et al. | |
| 2014/0207802 A1* | 7/2014 | Raghavan | G06F 16/9024 707/749 |
| 2017/0193173 A1 | 7/2017 | Miller | |

OTHER PUBLICATIONS

Centers for Disease Control and Prevention, "IIS Deduplication", National Center for Immunization and Respiratory Diseases, Dec. 12, 2012, 1 page.

Bradley et al., "Health Services Research and Data Linkages: Issues, Methods, and Directions for the Future". http://www.ncbi.nlm.nih.gov/pmc/articles/PMC2965887/. Health Services Research. Health Research and Educational Trust, 2010, 7 pages.

Wilson et al., "The benefit of using both claims data and electronic medical record data in health care analysis", https://www.optum.com/content/dam/optum/resources/whitePapers/Benefits-of-using-both-claims-and-EMR-data-in-HC-analysis-WhitePaper-ACS.pdf, Optum White Paper, copyright 2012, 4 pages.

"Truven Health Analytics Links Clinical Data with Claims to Enhance Oncology Outcomes Research", http://truvenhealth.com/news-and-events/press-releases/detail/prid/33/Truven-Health-Analytics-Links-Clinical-Data-with-Claims-to-Enhance-Oncology-Outcomes-Research, Truven Health Analytics, 2014, 1 page.

Dusetzina SB, Tyree S, Meyer AM, Meyer A, Green L, Carpenter WR. Linking Data for Health Services Research: A Framework and Instructional Guide. (Prepared by the University of North Carolina at Chapel Hill under Contract No. 290-2010-000141.) AHRQ Publication No. 14-EHC033-EF. Rockville, MD: Agency for Healthcare Research and Quality; www.effectivehealthcare.ahrq.gov/reports/final.cfm. Sep. 2014, 88 pages.

AIRA Modeling of Immunization Registry Operations Workgroup (eds), "Vaccination Level Deduplication in Immunization Information Systems", http://www.cdc.gov/vaccines/programs/iis/technical-guidance/deduplication.html, American Immunization Registry Association (AIRA), Atlanta, GA, Dec. 7, 2006, 102 pages.

Fellegi et al., "A theory for record linkage." Journal of the American Statistical Association 64.328 (1969): 1183-1210, 2 pages.

List of IBM Patents or Patent Applications Treated as Related, Jun. 2017, 1 page.

"The Explorys Platform", IBM Watson Health, Solution Brief, Produced in the United States of America, Nov. 2015, 4 pages.

* cited by examiner

LINKING ENTITY RECORDS BASED ON EVENT INFORMATION

CROSS-REFERENCE TO RELATED APPLICATIONS

This application is a continuation of U.S. patent application Ser. No. 14/988,009, entitled "LINKING ENTITY RECORDS BASED ON EVENT INFORMATION" and filed Jan. 5, 2016, the disclosure of which is incorporated herein by reference in its entirety.

BACKGROUND

1. Technical Field

Present invention embodiments relate to data integration systems, and more specifically, data integration systems utilizing event-based information, such as medical information from specific events or encounters, to link entity records.

2. Discussion of the Related Art

Healthcare networks have very complicated organization structures. An organization typically comprises multiple source systems (e.g., a source of electronic medical records including electronic health records (EHR), records from a claims system, lab feed, various data sources implementing the HL7 standard, patient satisfaction survey, etc.). Moreover, clinically integrated networks (CIN) or galaxies (e.g., a group of organizations) are collections of individual healthcare systems. Within each source system, data may be input for various entities (e.g., patients, companies, etc.), perhaps based on forms that a patient fills out or documentation from a physician, for various events (e.g., outpatient procedure, hospital visit, insurance claim, laboratory test, etc.). Accordingly, various data objects in a source system may be associated with a common event for a common entity (e.g., a patient). For example, multiple data objects may be input or created for a single patient for a single event (e.g., documentation from two different departments of a hospital for a patient during a single hospital visit).

Accordingly, examining and associating records of the different healthcare systems with common entities may be complex, burdensome, and processing intensive (with respect to processing resources and processing time).

SUMMARY

According to one embodiment of the present invention, a system links data objects associated with a common event and includes at least one processor. The system compares data objects associated with an entity and corresponding to a plurality of events for the entity, wherein the data objects are stored within a plurality of different source systems. Candidate data objects associated with a common event for the entity are identified based on the comparing. The candidate data objects are linked to form a set of data objects representing the common event for the entity. Embodiments of the present invention further include a method and computer program product for linking data objects associated with a common event for an entity.

BRIEF DESCRIPTION OF THE DRAWINGS

Generally, like reference numerals in the various figures are utilized to designate like components.

DETAILED DESCRIPTION

An organization may comprise multiple source systems (e.g., a source of electronic medical records including electronic health records (EHR), records from a claims system, lab feed, various data sources implementing the HL7 standard, patient satisfaction survey, etc.), while clinically integrated networks (CIN) or galaxies (e.g., a group of organizations) are collections of individual healthcare systems with data sharing agreements. Present invention embodiments primarily pertain to matching patient records associated with common events (e.g., event-based matches) at a source system level. However, in some embodiments, present invention embodiments could be used to determine event-based matches within an organization, galaxy, or between galaxies if desired. Regardless of the level of the event based matching, linking records based on event-based information may create "resolved clinical events" that includes any available information associated with a particular event, such as a hospital visit.

Present invention embodiments provide several advantages. Generally, present invention embodiments support or improve data management and collaboration within a medical organization and/or between medical organizations. Consequently, present invention embodiments may increase the data that is available to medical professionals, thereby improving medical care and diagnoses. Moreover, linking data objects based on event-based matching may link insurance claim information, various billing information, laboratory tests, etc. so that many complicated processes associated with medical care can be streamlined for efficiency, effectiveness, and accuracy. Increasing the effectiveness and accuracy of these processes may, in turn, support complex data governance issues of an organization, galaxy, or across galaxies.

More specifically, a resolved clinical event allows more in depth analytics to be preformed on patient data and provides the fullest possible picture of a patient's situation during or at a given event. For example, present invention embodiments may enable deeper analysis of metrics that are typically done on an aggregate level, such as stratification of hospital volume versus cost by visit type. Moreover, present invention embodiments may allow multiple similar events happening in the same day to be distinguished from duplicate events included in various systems. For example, if a patient gets discharged from the emergency room, but returns to the emergency room soon thereafter because of a new accident or condition, present invention embodiments may be able to link all records (i.e., lab tests, office visit records, etc.) from the first visit while also differentiating the records associated with the two different visits. Still further, present invention embodiments may resolve inaccuracies associated with traditional system that only count unique days for a given type of event (i.e., only one visit to an emergency room per day).

The event-based matching is preferably implemented in a distributed computing environment as described below, and is highly scalable to billions of event records for patients or other entities. By way of example, billions of source event records may be processed in a short time interval (e.g., minutes, etc.) since comparisons are performed for a single patient or entity with a relatively small quantity of records. However, present invention embodiments are environment agnostic and may also be implemented in non-distributed computing environments if desired.

Figure 1:
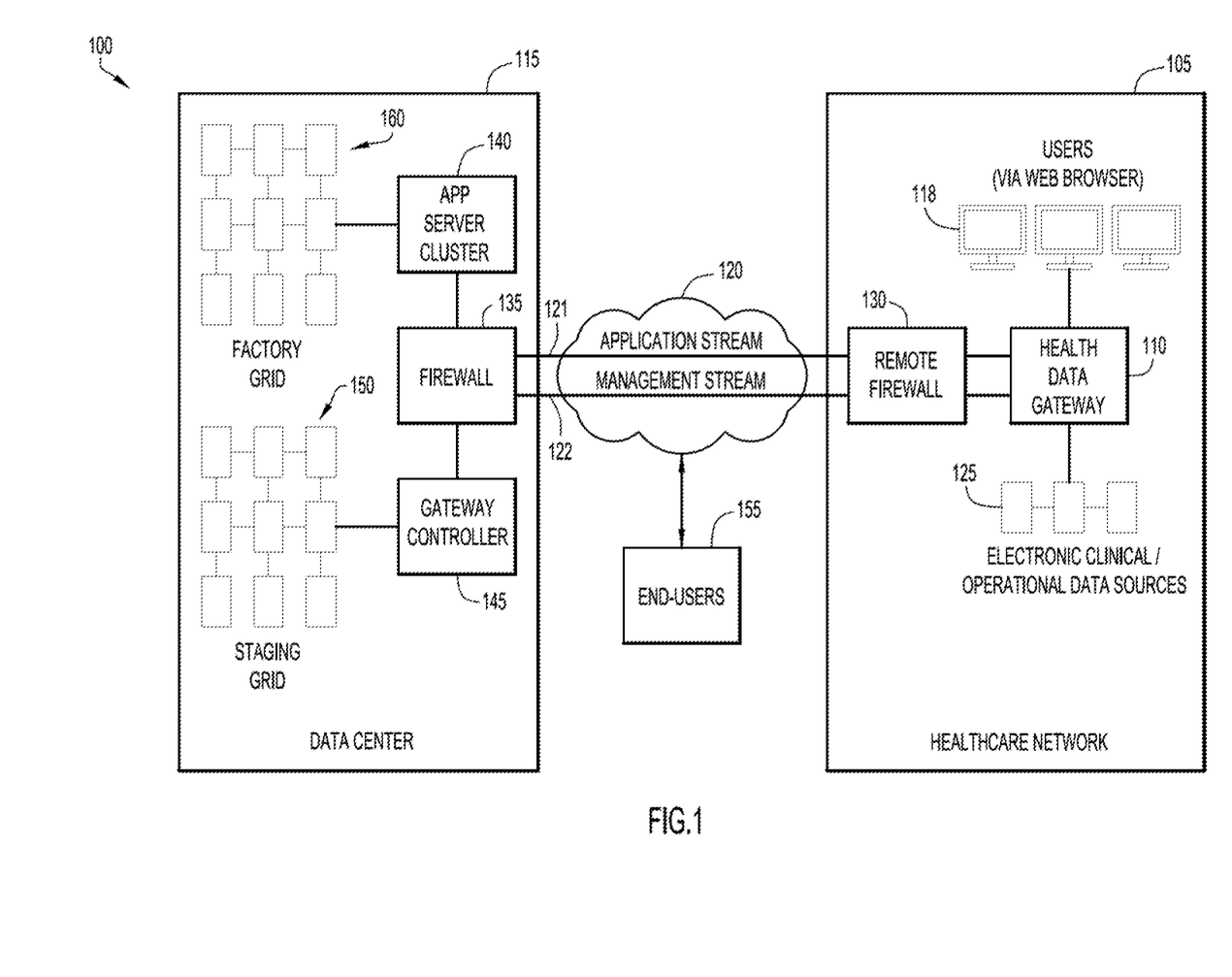
FIG. 1 is a diagrammatic illustration of an example computing environment according to an embodiment of the present invention.

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and communicate via any appropriate local communication medium (e.g., local area network (LAN), hardwire, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 105 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

Figure 2:
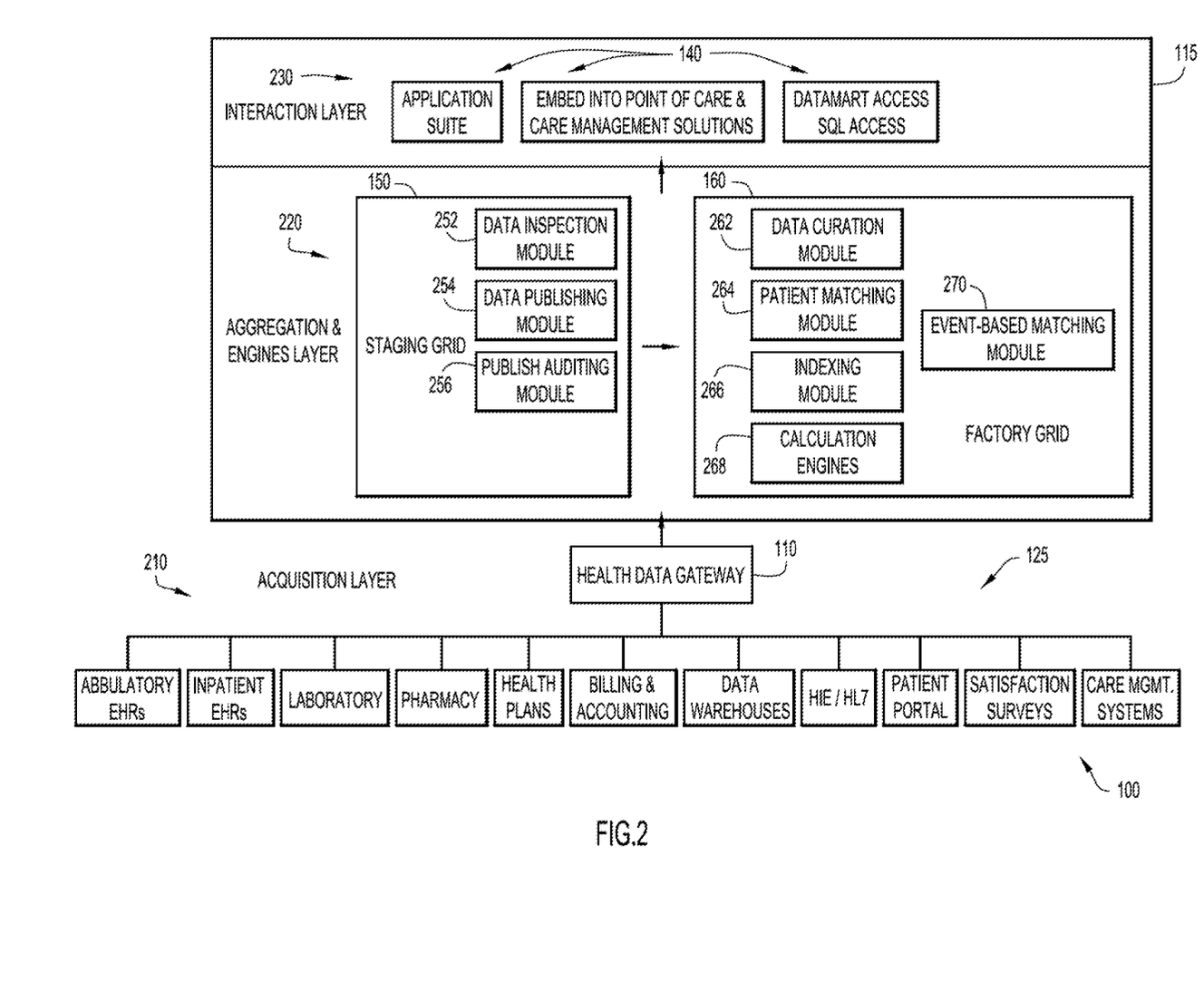
FIG. 2 is a diagrammatic illustration of the data center of the computing environment of FIG. 1 according to an embodiment of the present invention.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Factory grid 160 includes a data curation module 262, a patient matching module 264, an indexing module 266, various calculation/analytic engines 268, and an event-based matching module 270. Data curation module 262 performs data curation operations including mapping codes, data cleansing, and standardization, while patient matching module 264 performs patient matching operations to determine records associated with the same patient. Indexing module 266 performs indexing operations including combining records based on patient matching, mappings, and application of risk models. The calculation/analytic engines 268 perform the desired analytics based on queries received from end-users from an interaction layer 230 enabling application server cluster 140 to provide various applications for processing and accessing the data (e.g., analytic applications, SQL access, etc.). The staging and factory grids form an aggregation and engines layer 220 to process the acquired data, while the queries are handled by factory grid 160 in conjunction with application server cluster 140 to produce desired results for the interaction layer. The event-based matching module 270 performs matching operations to determine which patient records from a particular patient are associated with the same event.

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
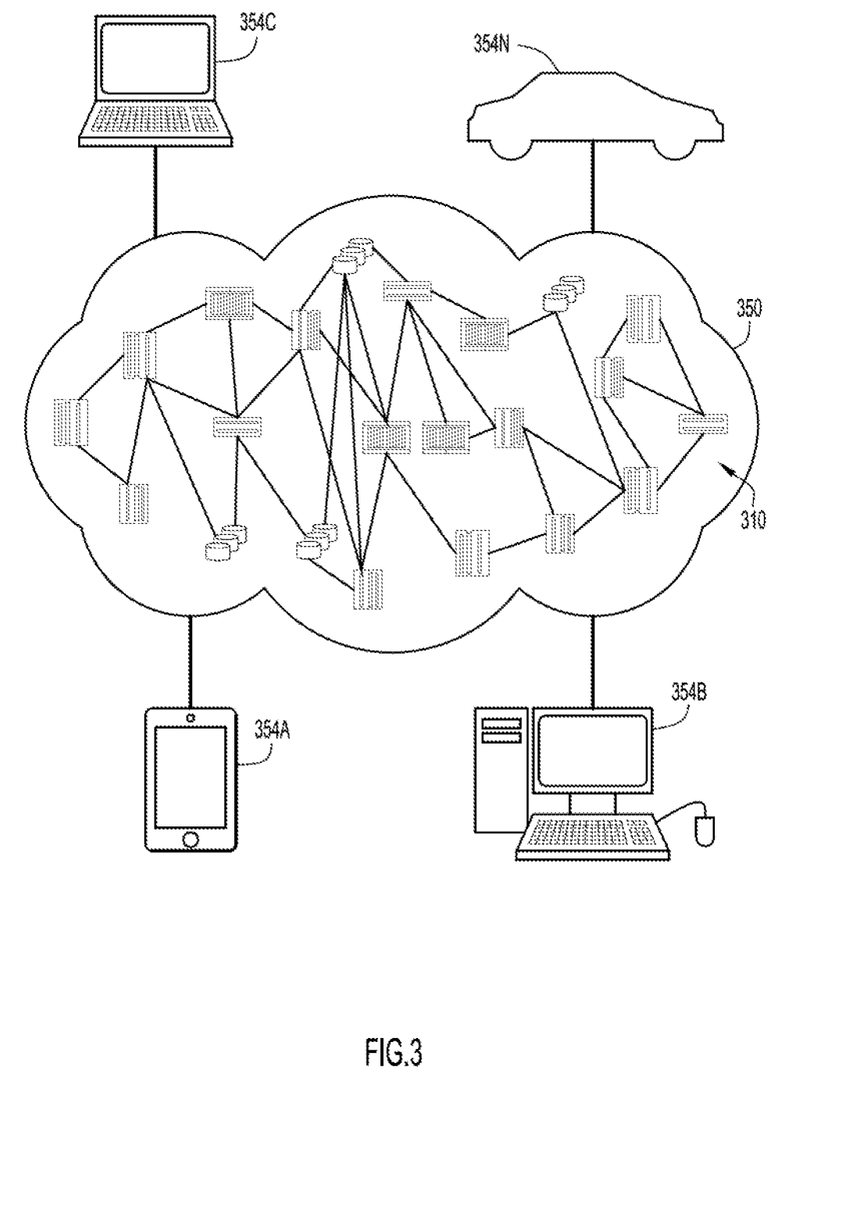
FIG. 3 is a diagrammatic illustration of an example cloud computing environment for the computing environment of FIG. 1 according to an embodiment of the present invention.

A cloud computing environment is service oriented with a focus on statelessness, low coupling, modularity, and semantic interoperability. At the heart of cloud computing is an infrastructure comprising a network of interconnected nodes. Referring now to FIG. 3, illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
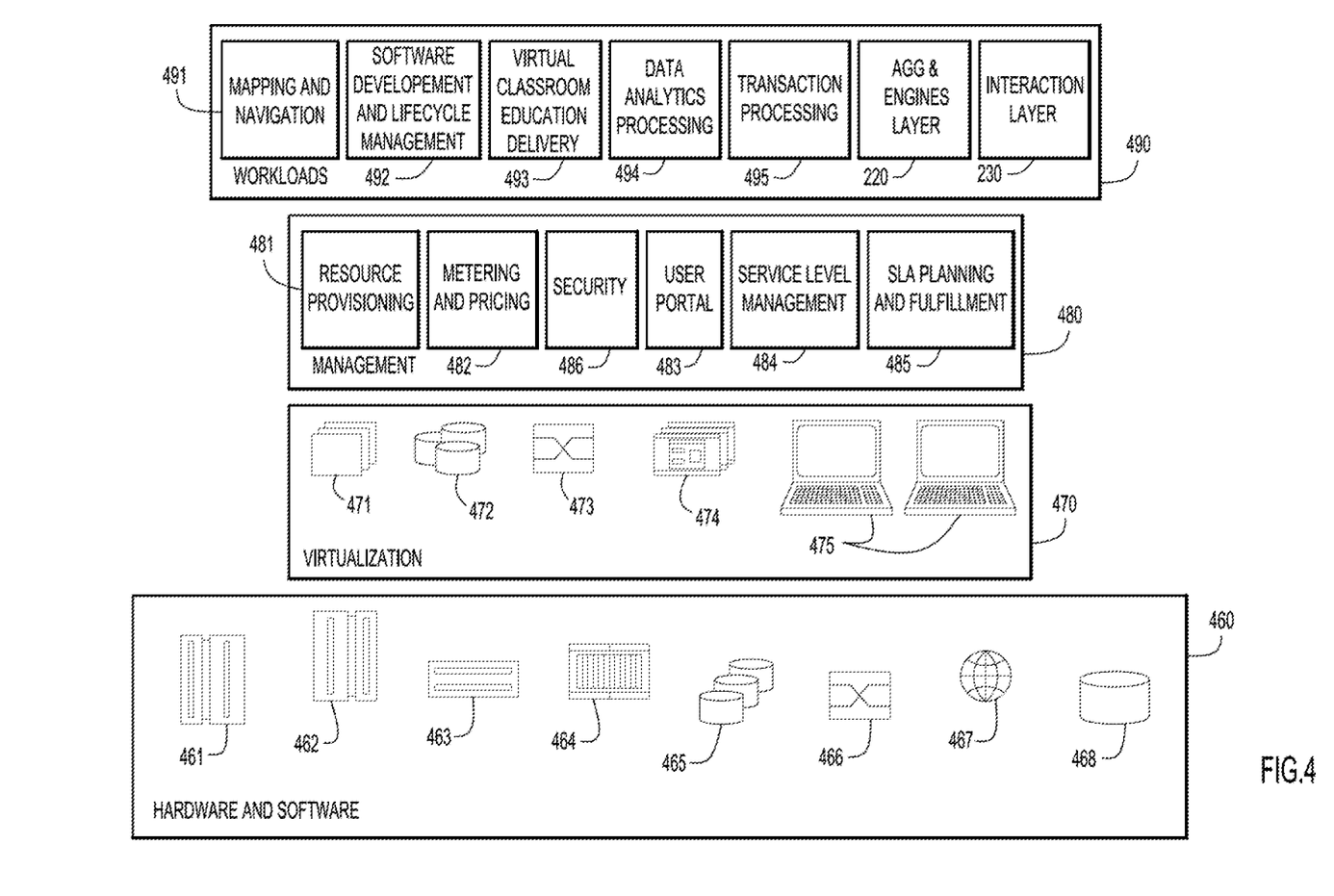
FIG. 4 is a diagrammatic illustration of abstraction model layers according to an embodiment of the present invention.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
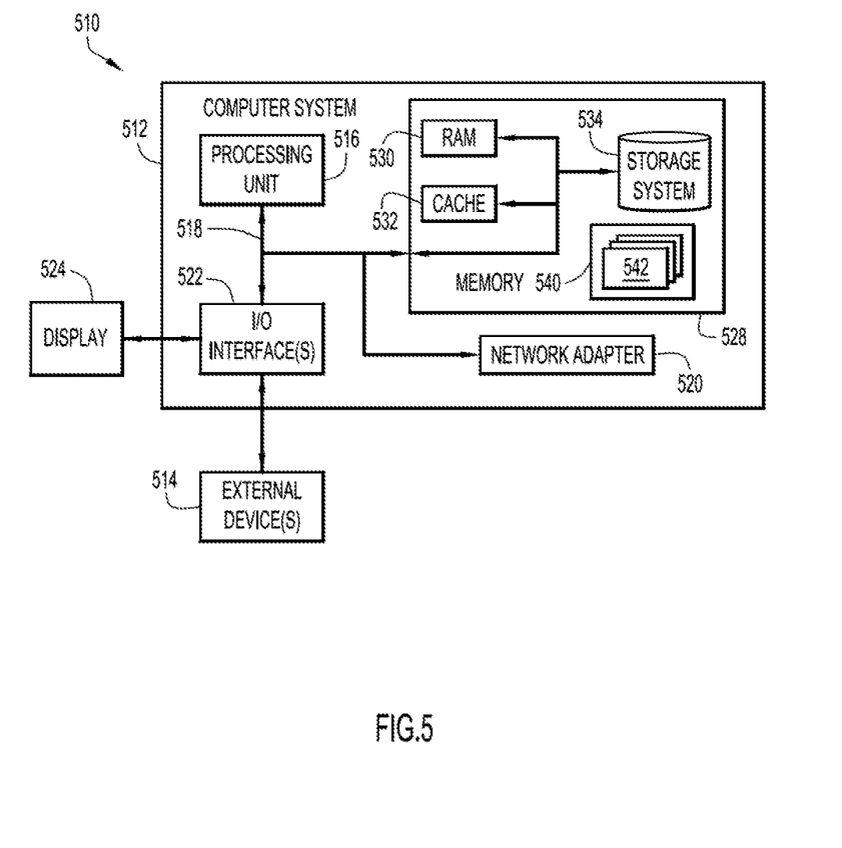
FIG. 5 is a block diagram of a computing node according to an embodiment of the present invention.

Referring now to FIG. 5, a schematic of an example of a computing node or device 510 of computer environment 100 (e.g., health data gateway 110, application server cluster 140, gateway controller 145, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510, there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

In FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

Figure 6:
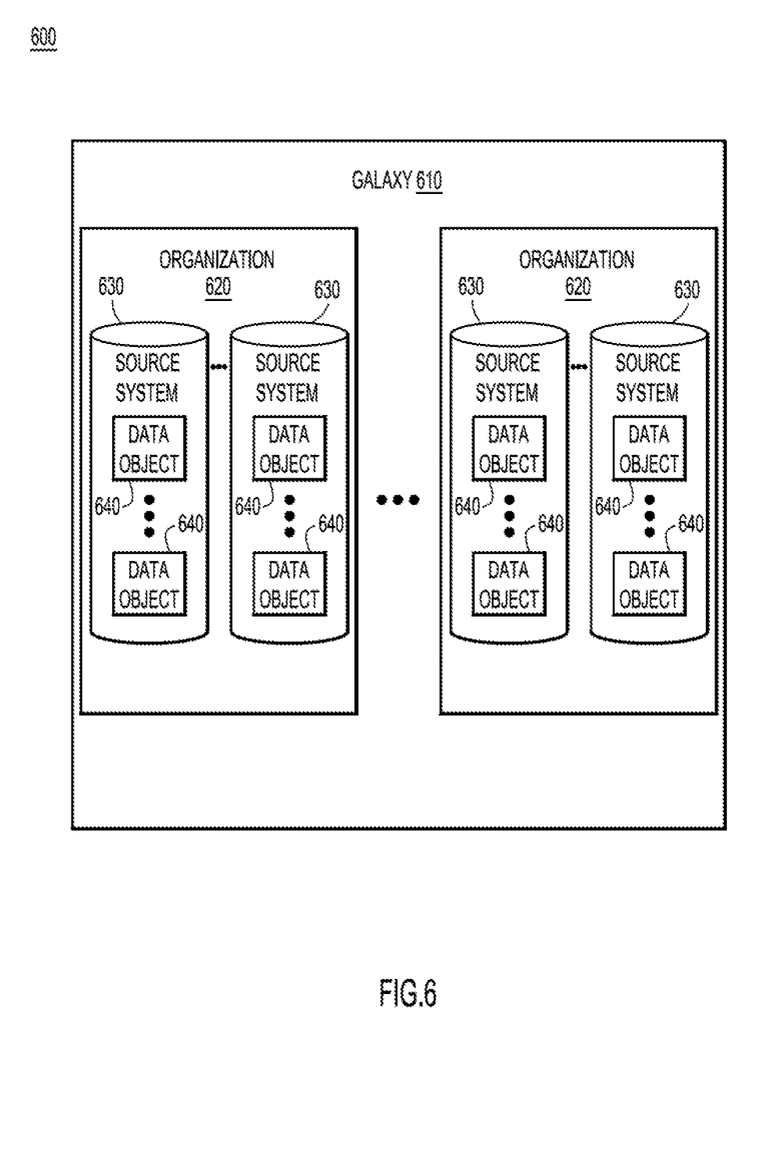
FIG. 6 is a block diagram illustrating the organization of data objects in a healthcare computing system according to an embodiment of the present invention.
Figure 7:
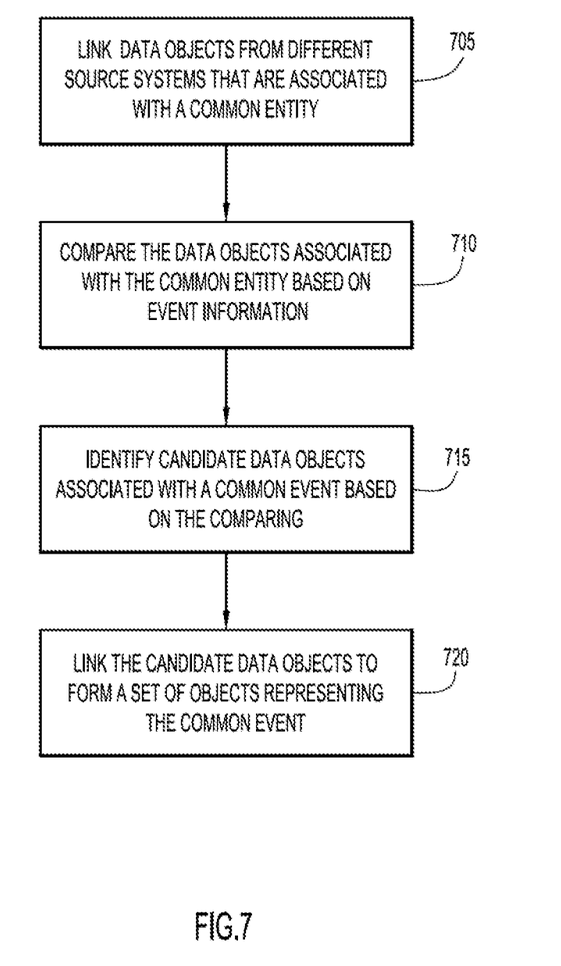
FIG. 7 is a procedural flowchart illustrating a manner of associating patient records with a common event according to an embodiment of the present invention.

A manner of associating or linking records of a common patient or other entity based on a common event (e.g., via the factory grid and event-based matching module 270) is illustrated in FIGS. 6 and 7. Initially, data objects 640 may be distributed within a source system 630 of an organization 620 (which may in turn be part of a galaxy 610). By way of example, each source system 630 contains medical or other records associated with patients and events and, in particular, data generated by or during human interactions regarding healthcare events. For example, source systems 630 may correspond to source systems 125 described above (FIG. 2). However, source systems 630 may contain any types of records, and the system may identify records associated with any type of desired event (e.g., hospital visit, laboratory test, insurance claim, etc.) for any desired entity (e.g., person, corporate or other business entity, healthcare or other medical related entity, healthcare provider, etc.) in substantially the same manner described below.

In embodiments associated with medical information, each patient record is associated with an event. Generally, the event-based matching process may employ various matching algorithms to determine a group of records of the source systems 630 associated with the same event for each patient of the source systems 630. In other words, all information available for a given patient is retrieved from every available system and linked in order to form a resolved clinical event.

Now referring to FIG. 7, initially at step 705, data objects associated with a common entity are linked together. In some embodiments, data objects within a single source system 630 may be linked together; however, in other embodiments, data objects associated with a common entity (i.e. a patient) may be linked across source systems 630. As an example, the patient matching process may employ various matching algorithms to determine for each patient of a source system 630 a group of records of the source system associated with that patient. In one particular example, the patient matching process may include a data pre-processing stage to clean and standardize any data, a blocking stage to divide the data into manageable portions with similar data, and a matching stage to further analyze and match patient records within the blocks that are associated with the same patient. In some of these embodiments, the patient matching process may also include a compacting stage and/or a splitting stage that may further parse, organize or otherwise refine the determined matches. Additionally or alternatively, the patient matching may be performed in a hierarchal manner, such that matches are found within a source system before matches are found between source systems, and so forth, in order to find records associated with a common patient within and across galaxies. In some of these embodiments, each of the patient matching stages may be performed as a respective MapReduce job within the distributed computing environment of factory grid 160 (FIG. 2). However, in other embodiments, any desirable record linkage algorithm may be applied to the data objects included in the source systems 630 in order to perform patient matching.

After patient matching is performed for each source system 630, the records associated with a common patient can be compared based on the event-based information included therein at step 710. In particular, the patient records associated with a single patient are compared to each other in a pairwise fashion to determine a likelihood score for the pair of records. The likelihood score may indicate whether or not the two records are associated with the same event, as opposed to simply categorizing or classifying the records. For example, if the likelihood score exceeds a similarity threshold, the patient records are linked and associated with the same event. Meanwhile, if the likelihood score is beneath the similarity threshold, the records are associated with different events.

The pairwise comparisons may focus on event-based information in order to determine if a particular pair of records is associated with the same event and, thus, event-based information may have a larger impact on the likelihood score than other information included in patient records. Event-based information may include a variety of fields or features, such as dates (can be a singular date or a range), locations, providers seen, procedures performed, diagnoses given, lab tests ordered, medications prescribed or filled, or any other desirable fields. However, additional information may also be considered when determining the likelihood score for two records. In some embodiments, all available contextual information is considered in order to ensure accuracy.

Each feature is associated with different matching levels for a comparison. Each matching level for a feature comparison has a corresponding associated weight. The associated weights for the matching levels indicate a likelihood the patient records are associated with the same or common event based on the level of matching of the corresponding feature or record field. The weights for the matches may be added to produce the likelihood score. When the likelihood score is greater than the similarity threshold, the patient records are linked and associated with the same patient. If the likelihood score is less than a difference threshold, the patient records are split or disassociated with one another.

Higher valued weights (and hence, a higher likelihood score) may indicate a greater likelihood of the patient records being associated with the same or common event. However, the magnitude of the weight values (and likelihood score) may be associated with any desired degree of likelihood of association of the patient records with a common event (e.g., greater likelihood, less likelihood, etc.). In addition, the similarity and difference thresholds may be set to any desired values to control the sensitivity or degree of matching needed to associate or link patient records with a common event. By way of example, some features may be associated with different matching levels as follows:

a date feature may be associated with matching levels of exact match, one day off, no information (e.g., one record omits a date), and mismatch (e.g., no match);

a location feature may be associated with matching levels of exact match, nearby match, same city match, same state match, typographical match, no match, and/or matching levels associated with different increments of distance;

a procedures performed feature may be associated with matching levels of exact match, no information, and no match;

a diagnosis feature may be associated with matching levels of primary diagnosis match, variant level of diagnosis match, overlapping match, secondary diagnosis match, and other such variants; and a medications feature may be associated with matching levels of dosage match, prescription match, and medicine type match.

By way of example, in some embodiments, rules may be used to determine and or assign the various matching levels to the features of an event. Then, weights or values may be assigned to the various levels of matching and the weights may be included or considered in determining the likelihood score. As a specific example, the following rule may determine whether the date features of two records being compared provide no information (which may have a minimal impact on the likelihood score), provide a match (e.g., same date or between date ranges) (which may add a large value, such as 10, to the likelihood score), provide a one day off match (which may add a medium value, such as 5, to the likelihood score), or provide a mismatch (which may add a negligible value, such as 1 to the likelihood score):

```
if encounterDate1 is null or encounterDate2 is null:
    return NO_INFORMATION
if encounterDate1 == encounterDate2:
    return MATCH
if encounterDate1 isBetween(admissionDate2, dischargeDate2) or
encounterDate2
isBetween(admissionDate1, dischargeDate1):
    return MATCH
if daysBetween(encounterDate1, encounterDate2) == 1:
    return ONE_DAY_OFF
return MISMATCH
```

As another specific example, the following rule may be applied to determine whether the diagnosis features of two records being compared provide no information (which may have no impact on the likelihood score), provide a primary diagnosis match (which may add a large value, such as 10, to the likelihood score), or provide an overlapping diagnosis match (which may add a medium value, such as 5, to the likelihood score):

```
if primaryDiagnosis1 == primaryDiagnosis2:
    return PRIMARY_DIAGNOSIS_MATCH*
    RARITY_SCALING(primary Diagnosis1)
if intersection(diagnoses1, diagnoses2) > 0:
    return OVERLAPPING_DIAGNOSES *
    RARITY_SCALING(intersection (diagnoses1, diagnoses2))
return NO_INFORMATION
```

Notably, the matching levels for the diagnosis feature may not impact the likelihood score if there is no match since, unlike dates, diagnoses may frequently have no level of matching. Additionally, the value associated with the matches for diagnosis feature matches may also be multiplied by a rarity scaling factor which may increase the weight for rare diagnoses and decrease the weight for common diagnoses. However, the scaling factor may depend on environmental factors in order to account for regional outbreaks or other such circumstances which would impact the rarity of a particular diagnosis. More generally, any feature may be associated with different levels of matching that may impact the likelihood score in any manner due to the specific nature of that particular feature. However, as more features are considered, the overall impact from all of the features may increase the accuracy of the likelihood score. Accordingly, in some embodiments, all features from an event (e.g., a patient record) are considered.

Both during and subsequent to the comparison of features included in the various patient events (e.g., records or data objects), candidate data objects associated with a common event may be identified at step 715. Then, candidate objects determined to be associated with a common event may be linked to form a set of objects representing the common event at step 720. As an example, any events with a likelihood score exceeding a certain similarity threshold may be selected as candidate data objects and associated with the common event.

In addition, the resulting common events may be compared to identify candidate events through time associated with a common episode (or set of common events) for the patient or entity. The candidate events are linked to form a set of common events representing the common episode for the patient or entity. The features of the records of the common events may be compared to each other in substantially the same manner described above to determine likelihood scores for pairs of common events. Since a common event may contain a plurality of event records from different sources, the record fields may have varying values for the same field. In this case, the comparisons may be expanded to include the variants (or different record field values) from the common events. The maximum weight from a comparison of the feature or record field between records of each of the common events (e.g., in pairwise comparisons of records between the common events) is determined and used as the weight for that feature. For example, a highest attained matching level (associated with the greatest weight value) may be utilized for a particular feature. The weights for the features may be added to produce the likelihood score for the pair of common events. Common events with likelihood scores satisfying a similarity (or difference) threshold may be linked (or split) in substantially the same manner described above.

As a more specific example of comparing events, identifying candidates events, and linking candidate events to form a set of events for a common event, consider an example where a system includes three records for a specific patient, John Smith:

The first record is for an office visit (event type "office visit") on Mar. 19, 2013, and includes a diagnosis of Diagnosis Code 486, but not as a primary diagnosis. The first record also indicates that the rendering provider was Physician 1, the primary care provider was Physician 1, and the referring provider was Physician 2. Moreover, the first record has a record identification (ID) of 123 and is from source system EMR 1.

The second record is for an office visit (event type "office visit") on Mar. 19, 2013, and includes a diagnosis of Diagnosis Code 486 as a primary diagnosis. The second record also indicates that the rendering provider was Physician 1. However, the second record has a record ID of 456 and is from source system CLAIMS 1.

The third record is documentation (the event type is "documentation") on Mar. 18, 2013, and does not include a diagnoses. The record also indicates that the rendering provider was Physician 1, has a record ID of 789, and is from source system EMR 2.

In this example, the first record and the second record are identified as candidate objects and linked together because the event records share the same event type ("office visit"), date and provider. Additionally, the third record is also linked with the first and second records because the third record has the same provider on the day before the office visit, which typically indicates preparation for the office visit.

In another example, patient records can be linked if all of the records are for the same date and location and include related medical information. For example, if a patient enters the emergency room with chest pain, a record for imaging of the chest (i.e., an x-ray or magnetic resonance imaging (MRI)) may be linked with records from a physical examination performed by a resident physician, and blood work sent to a laboratory. Thus, all of the information associated with the examination of the symptom (chest pain) may be available and associated so a single physician can quickly get up to speed on the patient and have any possibly helpful information available. This may also enable a referral from a physician's office to the emergency department to be linked with any documents created by the emergency room, despite the emergency room and physician's office using different EMRs.

In yet another example, the present invention may be used to link records for claim information, which link financial data to clinical data. Frequently, claims systems include many different types of claims for even a single visit (e.g., a laboratory claim, a facility claim, a physician claim, medical equipment and/or drug claims, and any cancellations or adjustments). Consequently, linking financial claims may provide financial and insurance entities, as well as the patient, with an overview of the claims process for a single event.

In still other examples, present invention embodiments may be applied to construct events including external lab systems, inpatient stays, and medical claims. Since external lab systems have very rich data about lab results with a lot of detail, but seldom have an explicit link to clinical systems, this may vastly increase the amount of data available to health care providers. Additionally or alternatively, linking records associated with common events to form resolved clinical events may enable healthcare administrators, such as information technology professionals, to perform sophisticated analysis on healthcare statistics and economics. For example, hospital volume versus cost or income could be stratified by visit type or event based risk scores. Moreover, information that is not explicitly linked, such as the cost of a hospital visit can be compared to a step count from a patient or provider, can be correlated in order to provide additional information about a hospital and allow workflow efficiency to be analyzed.

It will be appreciated that the embodiments described above and illustrated in the drawings represent only a few of the many ways of implementing embodiments for associating entity records based on event information.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, event-based matching module, etc.). These systems may include any types of monitors and input devices (e.g., keyboard, mouse, voice recognition, etc.) to enter and/or view information.

It is to be understood that the software (e.g., event-based matching module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., event-based matching module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., blocking or matching criteria, thresholds, etc.). The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may utilize data in any desired structure (e.g., records, data objects, data structures, etc.), and associate the data with any desired entity (e.g., person, corporate or other business entity, healthcare or other medical related entity, healthcare provider, etc.) and/or event.

The matching process may compare or match any quantity of records (e.g., individual records, groups of records, sets of groups, collections of sets, etc.) based on any desired criteria (e.g., any quantity or combination of record fields or features, etc.). Further, the matching criteria may be expanded in any fashion to account for additional information (e.g., increase variants or values provided for matching, expand matching types or levels, etc.). The likelihood score may include any quantity of any types of levels of matching (e.g., exact, partial, phonetic, typo, etc.). The weights may be assigned to the matching levels in any desired fashion, and include any values. The matching level associated with any desired weight (e.g., greatest weight, lowest weight, etc.) may be selected for a feature of a plurality of records (e.g., group of records, set of groups, collection of sets, etc.). The weights may be combined in any fashion to provide a likelihood score. The value of the likelihood score may be associated with any degree of similarity (e.g., a lesser likelihood score may indicate a greater chance for a match, a greater likelihood score may indicate a greater chance for a match, etc.).

The present invention embodiments may employ any number of any type of user interface (e.g., Graphical User Interface (GUI), command-line, prompt, etc.) for obtaining or providing information (e.g., queries, analytic results, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for associating data from various data systems with any type of common entity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method of linking data objects associated with a common event for an entity comprising:
    comparing data objects associated with an entity and corresponding to a plurality of events for the entity, wherein the data objects are stored within a plurality of different source systems, wherein data objects are compared in a pair-wise fashion to determine a likelihood score that indicates a likelihood of compared data objects being associated with a common event, wherein determining the likelihood score comprises comparing information in fields of the data objects pertaining to one or more from a group of: dates, locations, healthcare providers, medical procedures, medical diagnoses, laboratory tests, and medications, wherein each field is associated with one or more weight values corresponding to one or more matching levels of the information in the field, wherein higher weight values are associated with higher matching levels of the compared information in the fields of the data objects, and wherein the likelihood score is determined by adding one or more weight values determined according to the one or more matching levels of the information in the fields of the compared data objects;
    identifying candidate data objects associated with a common event for the entity based on the comparing, wherein candidate data objects are identified as associated with a common event based on the likelihood score exceeding a threshold, and wherein the common event includes one of a stay at a medical facility, an external laboratory test, and a medical insurance claim; and
    linking the candidate data objects to form a set of data objects, wherein each of the linked candidate data objects in the set of data objects is associated with the common event for the entity.

2. The computer-implemented method of claim 1, wherein the entity includes a patient.

3. The computer-implemented method of claim 1, further comprising:
    identifying candidate events through time associated with a common episode for the entity; and
    linking the candidate events to form a set of events representing the common episode for the entity.

4. The computer-implemented method of claim 1, wherein the set of data objects form a resolved clinical event.

* * * * *